United States Patent [19]  [11] 4,034,124
van Dam  [45] July 5, 1977

[54] EMULSIONS

[75] Inventor: Antonius Franciscus van Dam, Vlaardingen, Netherlands

[73] Assignee: Lever Brothers Company, New York, N.Y.

[22] Filed: Nov. 19, 1975

[21] Appl. No.: 633,336

[30] Foreign Application Priority Data
Nov. 25, 1974 United Kingdom ............ 50958/74

[52] U.S. Cl. .............................. 426/602; 426/603; 426/605; 426/589; 426/662; 252/308; 252/356
[51] Int. Cl.² ...................... A23D 3/00; A23D 5/00
[58] Field of Search ............ 426/20, 34, 41, 46, 426/47, 602, 605, 662, 42, 589, 599, 603; 195/2, 3, 27, 30; 252/308, 310, 312, 356

[56] References Cited
UNITED STATES PATENTS
3,652,397  3/1972  Pardun .......................... 426/662 X OTHER PUBLICATIONS
Frutton, J. S. et al., "General Biochemistry", John Wiley & Sons, Inc., New York, 1953, pp. 56, 57, 506, 507.

Primary Examiner—Raymond N. Jones
Assistant Examiner—R. A. Yoncoskie
Attorney, Agent, or Firm—Melvin H. Kurtz

[57] ABSTRACT

Emulsions comprising an oil phase, an aqueous phase and a phospholipo-protein which has been subjected to a treatment with phospholipase A as emulsion stabilizer. These emulsions have an increased stability, especially heat stability, compared with emulsions which do not contain such a stabilizer.

17 Claims, No Drawings

EMULSIONS

This invention relates to emulsions comprising an oil phase and an aqueous phase, more particularly oil-in-water emulsions which contain an emulsion stabilizer.

It is known to use e.g. egg yolk as an emulsifying agent, for instance for the preparation of mayonnaise. However, emulsions stabilized by egg yolk, like mayonnaise, cannot be heat-sterilized because the emulsion will break during heating to sterilization temperatures. Consequently the pH of emulsions stabilized by egg yolk often has to be lower than dictated by mere taste requirements in order to obtain satisfactory microbiological storage stability.

In Dutch Patent Application 6,809,971 the perparation of stabilized oil-in-water emulsions is described. Stabilization of the emulsions is achieved by the use of a monoacyl glycerophosphatide. The monoacyl glycerophosphatide can be synthesized or be prepared by subjecting the diacyl glycerophosphatide to the action of phosholipase A derived from pancreatin. The emulsions contain preferably a small amount of a protein such as casein or a protein derived from soy. These proteins contain phospholipo-proteins.

The use of such unmodified phospholipo-protein plus an amount of modified phospholipids which are not complexed with protein has the disadvantage that it does not lead to heat-stable emulsions (compare Example IV of the present specification).

Japanese Patent Application 56,456 — 1962 describes a process for the preparation of a butter-like foodstuff using egg yolk or whole eggs which have been treated with an extract from *Aspergillus niger, Rhizopus chinensis* or *Aspergillus oryzae*, until the heat coagulation properties of the egg-protein disappear due to hydrolysis of the protein molecules.

The enzyme extract contains among other enzymes, lecithianases which are held responsible for the decomposition of lecithin in lysolecithin and are reported to produce a characteristic flavour. The modified eggs or egg yolks are mixed with an edible oil and an emulsifier such as sorbitol monomyrisate to give the butterlike product. For the preparation of stable emulsions a rather considerable amount of the emulsifier is used. Applicants used egg yolks or whole eggs modified according to the procedure described in the above Japanese publication for the preparation of oil-in-water emulsions. All attempts for preparing heat-stable emulsions failed. Consequently it can be said that the enzyme extract obtained according to the Japanese publication is only able to effect the flavour of the composition but is unable to stabilize oil-in-water emulsions.

It has now been found that oil and water emulsions, especially oil-in-water emulsions, having an improved stability, especially heat stability, as compared with emulsions containing unmodified phospholipo-protein, can be prepared when a phospholipo-protein which has been modified by the action of phospholipase A is incorporated during some stage of the emulsion preparation.

The emulsions prepared according to the invention can have either the oil phase or the aqueous phase as the continuous phase, and are in this specification referred to as water-in-oil emulsions and oil-in-water emulsions, respectively. Oil-in-water emulsions are preferred. The latter type of emulsion means for the purpose of this specification continuous aqueous phases containing any amount of fat and/or oil in dispersed form. Examples of emulsions which come under this definition are edible products like phase inversion margarines, soups or sauces, natural or artificial fruit juices, mayonnaise, dressings, spreads on non-edible products such as toilet preparations like shampoos, bath additives and skin-care products. Preferred oil-in-water emulsions are emulsions containing between 20 and 90%, more preferably between 40 and 90%, particularly between 70 and 90% oil or fat-containing oil. By fat we means a triglyceride which is hard at room temperature. (All percentages given in this specification are percentages by weight unless indicated otherwise).

Examples of phospholipo-protein-containing substances are casein, skim milk, butter milk, whey, cream, soyabean, yeast, egg yolk, whole egg, blood serum and wheat proteins. Egg yolk is used preferably as source of the phospholipo-protein.

Egg yolk or other sources of phospholipo-protein can be subjected to the action of phospholipase A and the modified product is then incorporated in the products according to the invention.

It is also possible to isolate the phospholipo-protein froms its source, subject this protein to the action of phospholipase A and then incorporate the modified phospholipo-protein in the products according to the invention.

The expression "modified" applied to phospholipo-protein as used herein denotes any degree of conversion brought about by the action of phospholipase A. Phospholipase A is an enzyme which effects cleavage of the bond binding a fatty acid radical to the glycerol part of the phospholipid molecule, thereby replacing this fatty acid radical by an OH-group, which is called conversion. Phospholipase A is also active when the phospholipid is complexed with protein (and then called phospholipo-protein in this specification).

Phospholipases other than phospholipase A do not bring about the desired characteristics. A suitable source of phospholipase A is pancreatin which is preferably heat-treated, preferably under acidic conditions. The heat treatment is carried out at a temperature between 60° and 90° C for 3–15 minutes preferably at pH between 4 and 6.5. The enzyme composition thus obtained is substantially free from enzymatic activity other than that resulting from phospholipase A, which is remarkably stable under the conditions of the above treatment. Another suitable source of phospholipase A is phospholipase A 10.000 from Nordmark Werke Hamburg which does not contain amylases, has a lipase activity of $0.8 \times 10^{-4}$ IU/mg and a proteolytic activity equivalent to 2.3% pure trypsine.

Phospholipids form a class of chemical compounds comprising as the main elements phosphatidylcholine and phosphatidylethanolamine and further some sphingomyelin, phosphatidylserine and phosphatidylinositol. All these compounds can form protein complexes.

The degree of conversion of modified phospholipo-protein is in this specification expressed as the percentage of converted phosphatidylcholine plus phosphatidylethanolamine based on the total amount of phosphatidylcholine plus phosphatidylethanolamine present before conversion. An easy method to obtain the figures required to compute this percentage is quantitative thin-layer chromatography.

The degree of conversion is determined inter alia by the temperature and pH at which and the period of time during which incubation of the phospholipoprotein with phospholipase A takes place as well as by the concentration of the enzyme and the presence of activating agents such as $Ca^{2+}$ ions or deactivating agents such as $Zn^{2+}$, $Cd^{2+}$, $Pb^{2+}$, EDTA, during this incubation.

It has been found that even a very low degree of conversion contributes to the emulsifying capacity of the modified phospholipo-protein as well as to the heat stability of the emulsion containing it. It has however also been found that the presence of unmodified phospholipo-protein is detrimental to the beneficial effects of the modified composition, without, however, totally off-setting these. Thus one would normally expect that replacing in an emulsion the entire modified phospholipo-protein content having a degree of conversion of say 40% by an equivalent amount of equal parts of unmodified phospholipo-protein and modified phospholipo-protein having a degree of conversion of 80%, would make no difference in the properties of the emulsion. It has been found, however, that the latter emulsion is appreciably less heat-stable than the former, although the latter emulsion is also appreciably better in this respect than an emulsion stabilized by an equivalent amount of unmodified phospholipo-protein.

It has been found that the degree of conversion should preferably be 10%. Particularly preferred emulsions according to the invention are emulsions in which the degree of conversion of the modified phospholipo-proteins contained therein is between 40% and 86%, especially between 50% and 60%. On the one hand a degree of conversion of 40% is easily attainable and on the other hand it ensures a very satisfactory emulsifying capacity and heat stability of the emulsion. Degrees of conversion higher than 60%, although excellently suitable, are somewhat less easy to obtain.

The use of modified phospholipo-protein produces results which are also strikingly different from those obtained following the procedure described in the prior art (compare Dutch Patent Application 6,809,971) where unmodified phospholipo-protein plus an amount of modified phospholipids which are not complexed with protein are used. Even when amounts of converted phospholipids were added corresponding to the addition of large amounts of modified phospholipo-protein with a very high degree of conversion, the results were still very disappointing in that the emulsions prepared broke down on heating. Preferred emulsions according to the invention are therefore emulsions in which substantially the entire phospholipid content is present in the form of phospholipo-protein which has been subjected to the action of phospholipase A.

The modification can be carried out under different conditions (temperature, incubation time, concentration of the enzyme etc.), which can easily be determined by the man skilled in the art. A proportion varying from 0.002 mg–0.2 mg phospholipase A per gram phospholipo-protein is suitable. This range holds for a phospholipase A composition having a specific activity of about 70 U/mg protein. 1U means that 1 microequivalent fatty acid is released per minute.

Modification with these phospholipases A leaves the phospholipid-protein complex intact. Careful isolation by centrifugation of lipo-protein fractions from modified and from unmodified egg yolk showed showed that the phospholipid part of modified egg yolk consisted of lyso-compounds, in other words the modification takes place in situ without splitting of the protein-lipid bond.

The quantity of modified phospholipo-protein which should be present in the emulsion can vary within very wide limits. This quantity is inter alia dependent on the composition of the emulsion, the presence of other emulsifying agents, the degree of conversion of the modified phospholipo-protein and the properties which are desired in the stabilized emulsion. The actual quantity to be used can easily be determined by those skilled in the art of stabilizing emulsions.

Proportions considerably lower than, sometimes 1/15 of those normally applied when using unmodified material, can be applied with comparable emulsifying efficiency when modified phospholipo-protein is used. Moreover, in the latter case the emulsions obtained are often heat-stable to a large degree.

As a general guideline according to the invention emulsions are preferred which contain between 0.05 and 5%, preferably between 0.5 and 4%, more preferably between 2 and 4% by weight of modified phospholipo-protein based on the oil (or fat-containing oil) content of the emulsion.

One of the special advantages of the emulsions according to the invention is that these emulsions have an improved heat-stability. By applying to a given emulsion, a certain minimum quantity of a modified phospholipo-protein having a given degree of conversion, it is possible to obtain emulsions which can withstand sterilization, e.g. at 100° C for 30 min., without losing their stability. This specific quantity can easily be ascertained by simple experiment. In a particularly preferred embodiment of the invention, emulsions are provided which have been sterilized. Hitherto in many instances it has been necessary to keep emulsions such as e.g. mayonnaise at a relatively low pH in order to ensure satisfactory microbiological stability. Emulsions according to the invention can easily have a pH between 4 and 6 and be made microbilogically stable by sterilization.

Furthermore, sterilized modified phospholipo-protein when used as an emulsion stabilizing agent imparts to the emulsion thus stabilized other advantages associated with heat stability. It is for instance possible to fill the emulsion in a hot condition into containers, thus obviating for these products the need for the special measures which have to be taken when these products are filled into containers at ambient temperature while maintaining sterility.

The stabilizing action obtained as a result of using the modified phospholipo-protein complex is not limited to the increase in heat-stability of emulsions from oil and water. In the preparation of mayonnaises or dressings the use of the modified phospholipo-protein complex makes it possible to start from a non-winterized oil and even from a hard fat-containing oil (compare Example VIII) and still get compositions which are stable under usual temperature conditions in a refrigerator.

Oil-in-water emulsions were prepared which contained 0.2–8% modified egg yolk (degree of conversion 10–90%), 0.5–98% water, 0.15–1.4% acetic acid, 0.8–83% of a glyceride oil (maize oil).

The oil used could even contain a certain amount of dry-fractionated palm oil fraction (olein fraction MP= 30° C). Stable emulsions containing 0.2–8% modified egg yolk (degree of conversion 10–90%), 0.5–98.3% water, 0.15–1.4% acetic acid, 0.8–60% dry fractionated palm oil fraction and 0–23% optionally winterized oil (maize) were obtained. Storage of the emulsions for several weeks at a temperature between 2° and 5° C followed by storage at 37° C did not show oil exudation.

It has further been found that the use of the modified phosphilipo-protein complex provides a possibility of increasing the alcohol content in emulsions. This has the advantage that the taste sensation of certain components, such as spices, is enhanced.

Preferred ranges for the ingredients of such oil-in-water emulsions are: 1-6% ethanol, 0.15-1.4% acetic acid, 0.2-8% modified egg yolk (degree of conversion 10-90%), 0.8-83% oil, 5-15% water. These emulsions have reasonable stability and taste.

An aspect of the present invention is an oil-in-water emulsion containing modified egg yolk which is substantially free of cholesterol.

Preferred ranges of the ingredients of such emulsions are: 0.2-8% modified egg yolk (degree of conversion 10-90%, which contained 0.02-0.18% cholesterol), 0.5-98.8% water, 0.15-1.4% acetic acid, 0.8-83% oil. These emulsions were found to be very stable at ambient temperature and during heating at 100° C for 30 minutes. Comparable emulsions prepared with unmodified egg yolk from which cholesterol had been extracted would break during the addition of oil.

The invention is illustrated by the following Examples:

EXAMPLE 1

In this Example, preserved egg yolk (92% egg yolk, 7% sodium chloride, 1% potassium sorbate) was treated with different enzymes in order to prove that the active component is phospholipase A. The enzyme-treated egg yolk was used to prepare in an Ultra-Turrax an oil-in-water emulsion of the following composition:

7.5 g egg yolk (38.5% of which are phospholipo proteins)
5 ml water
5 ml 10% acetic acid
80 g soybean oil The emulsion thus obtained was heated at 100° C for 30 min.

Pancreatin [ 4 × NF (National Formula) XII* ), pepsin (3.5 m Anson U/mg), papain (3.5 m Anson U/mg), trypsin (20,000 E/g), ficin (3.9 m Anson U/mg) and pronase E (70,000 PUK/g$^{x}$) were obtained from Merck, Darmstadt, Germany.

*) defined as being a substance containing enzymes, principally amylase, trypsin and lipase, converting not less than 100 times its own weight of NF potato starch reference standard, into soluble carbohydrates and not less than 100 times its own weight of casein into proteoses. 1 PUK (Protease Unit Kaken) effects an increase of absorption at 660 nm of the Folin-Ciocalteu colour reaction of 1.0 per minute in the TCA supernatant of casein after proteolysis at 40° C and pH 7.4 (Nomoto M & Narahashi Y, (1950). J. Biochem (Japan) 46, 653-67.

"Phospholipase A" in the table below denotes the solution obtained by heating a 5.2% pancreatin dispersion at 70° C for 6 min at a pH = 4. The heated dispersion was quickly cooled to 0° C and centrifuged at 3000 × g. The clear yellow solution (52 mg enzyme/ml) was used as such.

Phospholipase C and phospholipase D were obtained from Sigma International Ltd., St. Louis, Mo., U.S.A.

The results are given in Table I.

Table I

| Enzyme species and cofactor | Concentration enzyme per 60 g of egg yolk (mg) | Incubation Time (h) | pH | Temp. ° C | Stability of O/W emulsion after heating 10' at 100° C | Degree of conversion (%) |
|---|---|---|---|---|---|---|
| Papain with cystein ($5 \times 10^{-3}$ M) | 100 | 16 | 7.0 | 37 | broken after a few mins. | |
| Ficin with cystein ($5 \times 10^{-3}$ M) | 100 | 16 | 7.0 | 37 | " | |
| Pronase with cystein ($5 \times 10^{-3}$ M) | 100 | 16 | 7.0 | 37 | " | |
| Pepsin | 100 | 16 | 2.0 | 37 | " | |
| Trypsin | 40 | 16 | 6.5 | 37 | " | |
| Tryspin with desoxycholate | 140 140 | 16 | 6.5 | 37 | " | |
| Pretreated pancreatin | 1000 | 16 | 6.5 | 37 | stable | > 50 |
| Phospholipase A | 80 | 16 | 6.5 | 37 | stable | > 50 |
| Phospholipase C | 80 | 16 | 6.5 | 37 | broken | |
| Phospholipase D | 80 | 16 | 6.5 | 37 | broken | |

This table shows that only emulsions stabilized with egg yolk which had been treated with phospholipase A were heat-stable.

EXAMPLE 2

The phospholipose A solution from Example 1 was used to incubate egg yolk as described in Example 1 under varying conditions as shown in Table 2. The degree of conversion as defined before of the egg yolk obtained after each incubation is shown. The effect of the use of egg yolks of different degrees of conversion on the heat-stability of an emulsion as described in Example 1 is also shown.

Table 2

| Incubation Temp. (° C) | Time (h) | pH | Concentration enzyme 15 g egg yolk (mg) | Stability of 80% O/W emulsion after heating (30 min 100° C) | Degree of conversion (%) |
|---|---|---|---|---|---|
| 48 | 5 | 6.5 | 0.0 | broken | 0 |
| " | " | " | 2.0 | some stability left | 10 |
| " | " | " | 4.0 | " | 18 |
| " | " | " | 6.0 | some oil exudation | 26 |
| " | " | " | 8.0 | " | 33 |
| " | " | " | 10.0 | stable with slight oil exudation | 39 |
| " | " | " | 12.0 | " | 44 |
| " | " | " | 14.0 | " | 49 |
| " | " | " | 16.0 | stable | 54 |
| " | " | " | 18.0 | stable | 58 |
| " | " | " | 20.0 | stable | 62 |
| " | " | " | 40.0 | stable | 65 |
| 48 | 16 | 6.5 | 20.0 | stable | 86 |

This table shows that emulsions stabilized with modified egg yolk having degrees of conversion down to as low as 10% are improved with regard to heat stability. Modified egg yolk having degrees of conversion between 50 and 86% are shown to be very effective in imparting stability against severe heat treatment to emulsions prepared therewith.

EXAMPLE 3

Various emulsions as described in Example 1 were prepared with the exception, however, that the proportion of egg yolk was varied and that two different kinds of egg yolk were used, namely unmodifed egg yolk and egg yolk modified to a degree of conversion of 50%. The emulsions prepared were judged with regard to their stability before (at ambient temperature) and after sterilization for 30 min. at 100° C. The results are given in table 3.

Table 3

| Sample of egg yolk | Percentage egg yolk in emulsion | Properties at ambient temperature | after 30 min. at 100° C |
|---|---|---|---|
| unmodified | 1 | bad, oil exudation | broken |
|  | 2.5 | bad, oil exudation | broken |
|  | 5.0 | sufficient | broken |
|  | 7.5 | good | broken |
| modified | 0.5 | good | good |
|  | 1 | good | good |
|  | 2.5 | good | good |
|  | 5.0 | good | good |
|  | 7.5 | good | good |

This table shows that modification not only improves the heat stability of the emulsion prepared therewith but also improves the emulsifying properties of the egg yolk.

EXAMPLE 4

This example illustrates the results obtained when, instead of the modified phospholipo-protein complex according to the invention, a mixture of modified phospholipids and unmodified egg yolk is used. Emulsions as described in Example 1 were prepared in which the egg yolk was not modified but to which increasing amounts (0.25–1.25 g/7.5 g egg yolk) of modified phospholipids with a degree of conversion of 50% were added. After heating at 100° C for 30 min the emulsion prepared with the lowest concentration of modified phospholipid was totally broken; the others clearly showed oil exudation. Moreover, a bitter taste was clearly noticeable. The emulsion prepared with 1.25 g modified phospholipids contained three times the amount of converted phospholipids which could at most have been present if instead of unmodified egg yolk the same manner of modified egg yolk having a degree of conversion of 100% had been used. Nevertheless the result was much less satisfactory.

EXAMPLE 5

A phospholipo-protein fraction was isolated from soybeans. A solution containing 30% phospholipo-protein was tried to prepare an 80% oil-in-water emulsion as described in Example 1 while omitting the egg yolk, applying various amounts of the phospholipo-protein solution and making up for the balance with water. All efforts failed.

The phospholipo-protein was modified to a degree of conversion of 80% and when 16% (based on the oil content) of the 30%-solution was applied, the emulsion obtained was perfectly stable at ambient temperature and could be heated for 30 mins/at 100° C without losing its stability.

EXAMPLE 6

Two 80% oil-in-water emulsions as described in Example 1 were prepared, one having the egg yolk in unmodifed form, the other having the egg yolk in modified form with a degree of conversion of 80%.

Both emulsions were diluted with water, thus providing two series of emulsions with oil contents of 48%, 24%, 12%, 4% and 0.8% respectively. These diluted emulsions were subsequently heated at 100° C for 30 to 90 minutes.

The series of emulsions derived from the emulsion prepared with unmodified egg yolk showed severe oil exudation; the series of emulsions derived from the emulsion prepared with modified egg yolk, however, did not show any oil exudation whatever.

EXAMPLE 7

Preparation of a mayonnaise using a non-winterised oil.

In this experiment salted fresh whole egg (90.6% fresh whole egg, 8.7% sodium chloride, 0.7% sorbic acid) was treated with phospholipase a for 3 hrs at 55° C. The enzyme concentration was about 0.003%, based on whole egg. The modified whole egg was used to prepare, by means of a colloid mill, a mayonnaise of the following composition:

15.45 g salted fresh whole egg
3.8 g water
5.3 g vinegar
75.0 g non-winterized maize oil
0.045 g spices
0.40 g thickening agent The maize oil was not winterized and showed haze formation after storage for 5 hours at 0° C.

As blank sample a mayonnaise was prepared as described, with the exception that non-modified salted whole egg was used instead of modified salted whole egg. Both samples were stored for 5 weeks at 2° and 5° C respectively. After storage at 2° and 5° C the samples were stored for 24 hours at 20° C, followed by storage at 37° C for 2 hours. The samples were examined as to oil exudation and the increase of the mean diameter of the fat globules examined microscopically.

On microscopic examination it appeared that mayonnaise prepared with non-modified whole egg showed a strong increase in mean diameter (from 5 $\mu$ before storage to about 15–25 $\mu$ after storage) of the fat globules after storage at 2° and 5° C, 20° C and 37° C, whereas the mean diameter of the fat globules of mayonnaise prepared with modified whole egg was nearly the same before and after storage. The detailed results are given in Table 4. Oil exudation could not be observed visually in either of the samples.

Table 4

Mean diameter and extremes of fat globules of mayonnaise prepared with modified and non-modified whole egg before and after storage

| Storage conditions | Non-modified whole egg | Modified whole egg |
|---|---|---|
| before storage | 3–5 $\mu$ | 3–5 $\mu$ |
| 5 weeks at 2° C + 24 hrs at 20° C | 15 $\mu$ | 3–4 (max. 12–15 $\mu$) |
| 5 weeks at 2° C + 24 hrs at 20° C + 2 hrs at 37° C | 20–25 $\mu$ (max. 40 $\mu$) | 4–7 (max. 23 $\mu$) |
| 5 weeks at 5° C + 24 hrs at 20° C | 18 $\mu$ (max. 30 $\mu$) | 3 $\mu$ (max. 13 $\mu$) |
| 5 weeks at 5° C + 24 hrs at 20° C + 2 hrs at 37° C | 8–20 (max. 50 $\mu$) | 7 $\mu$ (max. 15 $\mu$) |

EXAMPLE 8

Preparation of a hard fat containing mayonnaise.

In this experiment salted fresh whole egg (90.6% fresh egg, 8.7% sodium chloride, 0.7% sorbic acid) was treated with phospholipase A for 3 hrs at 55° C. The enzyme concentration was about 0.004%, calculated on whole egg. The enzyme-treated whole egg was used to prepare in an Ultra Turrax an oil-in-water emulsion of the following composition:

15.45 g salted fresh whole egg
3.8 g water
5.3 g vinegar
75.0 g mixtures in different proportions of maize oil and dry-fractionated palm oil In the preparation of the samples, crude and refined dry fractionated palm oil fraction were heated to 60° C and mixed in different proportions with maize oil; the warm palm oil fraction-maize oil mixture was stirred with an Ultra Turrax into a water phase containing modified or non-modified whole egg, acetic acid and salt. The samples were stored for 3 weeks at 5° C. After storage the samples were heated to 20° C for 24 hrs, followed by heating to 37° C for 2 hrs and examined on oil-exudation.

Table 5 shows that the samples prepared with modified whole egg were stable under usual temperature conditions in a refrigerator stable even at a replacement of about 40% of maize oil by raw or refined dry fractioned palm oil. In contrast: all samples made with non-modified whole egg were not stable under usual temperature conditions in a refrigerator stable. Even the sample made with 100% maize oil was not stable under usual temperature conditions in a refrigerator stable, probably due to high temperature of the preparation of the sample. It is assumed that a replacement of 40% is near the limit of replacement. Probably with a palm oil fraction having a less steeper dilatation curve a higher replacement percentage can be reached.

It was found that by using modified whole egg, mayonnaise stable at usual temperature conditions in a refrigerator can be made in which 40% of maize oil has been replaced by dry fractionated palm oil.

found that by using unmodified egg yolk as emulsifier no stable 80% O/W emulsion could be made. During addition of the soybean oil to the water phase-containing alcohol, the emulsion broke after addition of a few milliliters of oil. With modified egg yolk as emulsifier a 80% O/W emulsion could be prepared which was stable before and after storage for 48 hours at 5° C followed by storage for 24 hours at ambient temperature. The taste of the alcohol containing mayonnaise was judged as good, compared with a sample containing no alcohol. A somewhat sweeter and more spicy taste was observed.

EXAMPLE 10

Preparation of emulsions by using modified egg yolk from which practically all the cholesterol had been removed.

Cholesterol was removed for 95-99 percent from spray-dried salted modified egg yolk and non-modified egg yolk by extraction with dichloromethane. In order to remove dichloromethane, the powder was dried in vacuo at a temperature of about 45° C for about 2 hours. With these dry powders two 80% oil-in-water emulsions as described in Example 1 were prepared, one having the egg yolk in unmodified form and the other having the egg yolk in modified form with a degree of conversion of 50% or higher. The emulsion prepared with the extracted non-modified egg yolk broke during the addition of oil; the other emulsion with the extracted modified egg yolk was stable at ambient temperature and during heating at 100° C for 30 minutes.

What we claim is:

1. A water and oil emulsion, which contains at least 0.05%, based on the quantity of oil, of a phospholipoprotein which has been modified by phospholipase A to a degree of conversion of at least 10%.

Table 5

| | Cold-stability of mayonnaise made with modified and non-modified whole egg and with different proportions of dry-fractionated palm oil and maize oil | | | | | | | |
|---|---|---|---|---|---|---|---|---|
| percentage dry fractionated palm oil fraction | whole egg | | | | modified whole egg | | | |
| | crude dry fractionated palm oil fraction | | refined dry fractionated palm oil fraction | | crude dry fractionated palm oil fraction | | refined dry fractionated palm oil fraction | |
| | stability at 20° C | stability at 37° C | stability at 20° C | stability at 37° C | stability at 20° C | stability at 37° C | stability at 20° C | stability at 37° C |
| 0 | sl.oil | much oil | sl.oil | much oil | stable | stable | stable | stable |
| 10 | broken | broken | much oil | broken | " | " | " | " |
| 20 | broken | broken | broken | broken | " | " | " | " |
| 23 | broken | broken | broken | broken | " | " | " | " |
| 27 | not determined | not determined | not determined | not determined | " | " | " | " |
| 30 | not determined | not determined | not determined | not determined | " | " | " | " |
| 33 | not determined | not determined | not determined | not determined | " | " | " | " |
| 36 | not determined | not determined | not determined | not determined | " | " | " | " |
| 39 | broken | broken | broken | broken | stable | stable | stable | stable |

EXAMPLE 9

Preparation of emulsions with an increased alcohol concentration.

Various emulsions as described in Example 1 were prepared with the exception, however, that 5 ml water were replaced by 5 ml 96% ethanol, that two different kinds of egg yolk were used, viz. non-modified egg yolk and egg yolk modified to a degree of conversion of 50% or higher, and that different spices were added. The emulsions prepared were assessed with regard to their stability before and after storage for 48 hours at 5° C followed by 24 hours at ambient temperature, and with regard to the taste of the emulsions prepared. It was 2. An emulsion according to claim 1, in which water constitutes the continuous phase.

3. An emulsion according to claim 1, in which the phosholipo-protein containing material is whole egg.

4. An emulsion according to claim 1, in which the phospholipo-protein containing material is egg yolk.

5. An emulsion according to claim 4, in which the phospholipo-protein containing material is egg yolk substantially free from cholesterol.

6. An emulsion according to claim 1, in which substantially all of the phospholipo-protein present therein has been subjected to the treatment with phospholipase A.

7. An emulsion according to claim 1, in which 0.05–5% modified phospholipo-protein based on the oil content of the emulsion is present.

8. An emulsion according to claim 1, in which the degree of conversion of the phospholipo-protein is from 40–60%.

9. An oil-in-water emulsion according to claim 1, which contains:
   0.2 – 8.0% egg yolk modified to a degree of conversion between 10 and 90%
   0.5 – 98.3% water
   0.15 – 1.4% acetic acid
   0.8 – 83% oil.

10. An emulsion according to claim 9, in which part of the oil has been replaced by fat.

11. An emulsion according to claim 10, which contains 0.8 – 60% of the olein fraction obtained by dry-fractionating palm-oil.

12. An emulsion according to claim 1, which contains:
   1–6% ethanol
   0.15–1.4% acetic acid
   0.2–8% egg yolk modified to a degree of conversion between 10 and 90%
   5–15% water
   0.8–83% oil.

13. An emulsion according to claim 4, which comprises:
   0.2–8.0% egg yolk modified to a degree of conversion between 10 and 90% and containing 0.02 to 0.18% cholesterol
   0.5–98.3% water
   0.15–1.4% acetic acid
   0.8–83% oil.

14. A process for the preparation of the emulsion set forth in claim 1, comprising treating a phospholipo-protein with a phospholipase A derived from pancreatin by subjecting to a heat treatment at a temperature from 60° to 90° C for a time sufficient to give a degree of conversion of at least 10%.

15. A process according to claim 14, in which the heat treatment is carried out for 3 to 15 minutes.

16. A process according to claim 14, in which the treatment is carried out at a pH from 4–6.5.

17. A process according to claim 14, in which per gram of phospholipo-protein 0.002–0.2 mg phospholipase A of specific activity of 70 U/mg protein is used.

* * * * *